US008784631B2

(12) United States Patent
Dolnik

(10) Patent No.: US 8,784,631 B2
(45) Date of Patent: Jul. 22, 2014

(54) SEPARATION MEDIUM FOR CAPILLARY ELECTROPHORESIS SUPPRESSING ELECTROOSMOTIC FLOW IN BARE CAPILLARIES AND CHANNELS

(76) Inventor: Vladislav Dolnik, Palo Alto, CA (US)

( * ) Notice: Subject to any disclaimer, the term of this patent is extended or adjusted under 35 U.S.C. 154(b) by 386 days.

(21) Appl. No.: 13/342,031

(22) Filed: Jan. 1, 2012

(65) Prior Publication Data
US 2013/0001084 A1   Jan. 3, 2013

Related U.S. Application Data

(60) Provisional application No. 61/437,760, filed on Jan. 31, 2011.

(51) Int. Cl.
*G01N 27/447* (2006.01)
(52) U.S. Cl.
CPC ................... *G01N 27/44747* (2013.01)
USPC ............................ 204/605; 204/601; 204/454

(58) Field of Classification Search
CPC ................. G01N 24/44747; G01N 24/44752; G01N 30/60; G01N 27/44747; G01N 27/44752
USPC .................................. 204/601, 605, 454, 455
See application file for complete search history.

(56) References Cited

U.S. PATENT DOCUMENTS

2004/0050702 A1 *  3/2004  Liu et al. ....................... 204/469

* cited by examiner

*Primary Examiner* — J. Christopher Ball

(57) ABSTRACT

Disclosed herein is a composition of a separation medium and method of its use for electrophoresis in bare channels, either capillaries or chips, with suppressed electroosmotic flow, wherein various forms of boric acid are adsorbed on the wall of said separation channel, efficiently suppressing zeta potential of the wall of said bare channel. A composition of a sieving separation medium for electrophoresis of DNA is disclosed. A composition of a sieving separation medium for electrophoretic size separation of proteins by SDS CSE is also disclosed. A composition of a separation medium for capillary electrophoresis without sieving is also disclosed.

22 Claims, 16 Drawing Sheets

SEPARATION MEDIUM FOR CAPILLARY ELECTROPHORESIS SUPPRESSING ELECTROOSMOTIC FLOW IN BARE CAPILLARIES AND CHANNELS

This application claims the benefit of the provisional application 61/437,760 filed on Jan. 31, 2011.

REFERENCES CITED

U.S. Patent Documents:
1) U.S. Pat. No. 4,925,545 Method of generating pH functions in electrophoresis and isoelectric focusing
2) U.S. Pat. No. 5,212,299 Glyceryl agarose and borate compositions
3) U.S. Pat. No. 5,314,595 Electrophoresis of nucleic acid fragments
4) U.S. Pat. No. 5,599,433 Capillary electrophoresis of glycosylated proteins
5) U.S. Pat. No. 5,567,292 Polymers for separation of biomolecules by capillary electrophoresis
6) U.S. Pat. No. 5,753,094 Borate storage buffer and sample diluent
7) U.S. Pat. No. 5,830,642 Electrophoresis of nucleic acid fragments
8) U.S. Pat. No. 5,849,166 Electrophoresis of nucleic acid fragments
9) U.S. Pat. No. 5,599,433 Capillary electrophoresis of glycosylated proteins
10) U.S. Pat. No. 6,410,668 Robust polymer coating
11) 20040050702 Methods and compositions for capillary electrophoresis (CE)
12) 20040222095 DNA separation using linear polymer solutions with dimethyl sulfoxide
13) 2008079217 Capillary sieving electrophoresis with a cationic surfactant for size separation of proteins
14) Ser. No. 12/359,345 Capillary sieving electrophoresis with a cationic surfactant for size separation of proteins
15) 20090166200 Serum components that bind to threat agents
16) 20090314638 Methods and Compositions for Capillary Electrophoresis Other References:
1) A. K. Varshneya, Fundamentals of Inorganic Glasses, Academic Press, Boston 1994.
2) M. van Duin, J. A. Peters, A. P. G. Kieboom and H. van Bekkum, Studies on borate esters I. The pH dependence of the stability of esters of boric acid and borate in aqueous medium as studied by $^{11}$B NMR. Tetrahedron 40 (1984) 2901-29141.
3) M. J. Taylor, J. A. Grigg anf I. H. Laban, Triol borates and aminoalcohol derivatives of boric acid: Their formation and hydrolysis. Polyhedron 15 (1996) 3261-3270.
4) A. Sonoda, N. Takagi, K. Ooi, T. Hirotsu, Complex formation between boric acid and triethanolamine in aqueous solutions. Bull. Chem. Soc. Jpn 71 (1998) 161-166.
5) J. Yan, G. Springsteen, S. Deeter, B. Wang, The relationship among $pK_a$, pH, and binding constants in the interaction between boronic acids and diols- it is not as simple as it appears. Tetrahedron 60 (2004) 11205-11209.
6) G. V. Troitsky, V. P. Zav'yalov, I. F. Kirjukhin, V. M. Abramov and G. Ju. Agitsky, Isoelectric focusing of proteins using a pH gradient created by a concentration gradient of nonelectrolytes in solution. Biochim. Biophys. Acta 400 (1975) 24-31.
7) S. A. Shukun, A. V. Gavryushkin, V. N. Brezgunov, and V. P, Zav'yalov, Protein separation in pH gradients using free-flow electrophoretic apparatus. II. The pH gradients formed by the concentration gradient of boric acid in solutions of borax and mannitol. Electrophoresis 6 (1985) 75-77.
8) S. Honda, S. Suzuki, A. Nose, K. Yamamoto and K. Kakehi, Capillary zone electrophoresis of reducing mono- and oligo-saccharides as the borate complexes of their 3-methyl-1-phenyl-2-pyrazolin-5-one derivatives. Carbohydrate Res. 215 (1991) 193-198.
9) S. Hoffstetter-Kuhn, A. Paulus, E. Gassmann, and H. M. Widmer, Influence of borate complexation on the electrophoretic behavior of carbohydrates in capillary electrophoresis. Anal. Chem. 63 (1991) 1541-1547.
10) M. Stefansson, M. Novotny, Separation of Complex Oligosaccharide Mixtures by Capillary Electrophoresis in the Open-Tubular Format. Anal. Chem. 66 (1994) 1134-1140.
11) J. P. Landers, R. P. Oda, M. D. Schuchard, Separation of boron-complexed diol compounds using high-performance capillary electrophoresis. Anal. Chem. 64 (1992) 2846-2851.
12) J. Plocek, and J. Chmelik, Separation of disaccharides as their borate complexes by capillary electrophoresis with indirect detection in visible range. Electrophoresis 18 (1997) 1148-1152. J. P. Quirino and S. Terabe, Sweeping of neutral analytes via complexation with borate in capillary zone electrophoresis Chromatographia 53 (2001) 285-289.
14) S. Weitzman, V. Scott and K. Keegstra, Analysis of glycopeptides as borate complexes by polyacrylamide gel electrophoresis. Anal. Biochem. 97 (1979) 438-449.
15) A. C. Peacock, C. W. Dingman, Resolution of Multiple Ribonucleic Acid Species by Polyacrylamide Gel Electrophoresis. Biochemistry 6 (1967) 1818-1827.
16) P. Carninci, S. Gustincich, S. Bottega, C. Patrosso; G. Del Sal, G. Manfioletti, C. Schneider, A simple discontinuous buffer system for increased resolution and speed in gel electrophoretic analysis of DNA sequence. Nucleic Acid Res. 18 (1990) 204-208.
17) M. Strege and A. Lagu, Separation of DNA restriction fragments by capillary electrophoresis using coated fused silica capillaries. Anal. Chem. 63 (1991) 1233-1236.
18) R. L. Brumley and L. M. Smith, Rapid DNA sequencing by horizontal ultrathin gel electrophoresis. Nucl. Acids Res. 19 (1991) 4121-4126.
19) J. Bashkin, M. Marsh, D. Barker, R. Johnston, DNA sequencing by capillary electrophoresis with a hydroxyethylcellulose sieving buffer. Appl Theor Electrophor. 6 (1996) 23-28.
20) J. J. Schwinefus, V. A. Bloomfield, The greater negative charge density of DNA in Tris-borate buffers does not enhance DNA condensation by multivalent cations. Biopolymers 54 (2000) 572-577.
21) N. C. Stellwagen, C. Gelfi and P. G. Righetti, DNA and buffers: the hidden danger of complex formation. Biopolymers 54 (2000) 137-142.
22) P. G. Righetti, C. Gelfi and M. R. d'Acunto, Recent progress in DNA analysis by capillary electrophoresis. Electrophoresis 23 (2002) 1361-1374.
23) J. R. Brody and S. E. Kern, Sodium boric acid: a Tris-free, cooler conductive medium for DNA electrophoresis, BioTechniques 36 (2004) 214-216.
24) K. L. Buchmueller and K. M. Weeks, Tris-borate is a poor counterion for RNA: a cautionary tale for RNA folding studies. Nucleic Acid Res. 32 (2004) e 184.
25) H. Singhal, Y. R. Ren and S. E. Kern, Improved DNA Electrophoresis in conditions favoring polyborates and Lewis acid complexation. PLOS one 5 (2010) e11318.

26) J. F. Poduslo, Glycoprotein molecular-weight estimation using sodium dodecyl sulfate-pore gradient electrophoresis: Comparison of Tris-glycine and Tris-borate-EDTA buffer systems. Anal. Biochem. 114 (1981) 131-139.
27) D. Wu and F. E. Regnier, Sodium dodecyl sulfate-capillary gel electrophoresis of proteins using non-cross-linked polyacrylamide, J. Chromatogr. A, 608 (1992) 349-356.
28) Y. Zhang, H. K. Lee and Sam F. Y. Li, Separation of myoglobin molecular mass markers using non-gel sieving capillary electrophoresis. J. Chromatogr. A 744 (1996) 249-257.
29) M. D. Harvey, D. Bandilla and P. R. Banks, Subnanomolar detection limit for sodium dodecyl sulfate—capillary gel electrophoresis using a fluorogenic non covalent dye. Electrophoresis 19 (1998) 2169-2174.
30) S. R. Bean and G. L. Lockhart, Sodium dodecyl sulfate capillary electrophoresis of wheat proteins. I. Uncoated capillaries J. Agric. Food Chem. 47 (1999) 4246-4255.
31) F. T. A. Chen, Rapid protein analysis by capillary electrophoresis. J. Chromatogr. A 559 (1991) 445-453).
32) B. A. Williams and G. Vigh, Determination of accurate electroosmotic mobility and analyte effective mobility values in the presence of charged interacting agents in capillary electrophoresis. Anal. Chem. 69 (1997) 4445-4451.
33) J. Horvath and V. Dolnik, Wall coatings in capillary electrophoresis. Electrophoresis, 22 (2001) 644-655.
34) K. Klepárnik Z. Malá, P. Boček, Fast separation of DNA sequencing fragments in highly alkaline solutions of linear polyacrylamide using electrophoresis in bare silica capillaries. Electrophoresis, 22 (2001) 783-788.

FIELD OF THE INVENTION

The present invention relates to electrophoretic separation in bare capillaries and channels, preferably under sieving conditions with suppressed electroosmotic flow. Specifically, the invention is directed to the composition of a background electrolyte comprising high concentration of boric acid and polyol bases containing several hydroxyl groups.

BACKGROUND OF THE INVENTION

Capillary Electrophoresis and Electroosmotic Flow

Capillary electrophoresis (CE) offers high-resolution separation of ionic analytes due to efficient heat dissipation. Typically, CE is performed in fused silica capillaries but may be performed in glass or plastic chips. Ionization of silanol groups results in generation of electroosmotic flow that is detrimental to high resolution separations and has to be suppressed by introducing static or dynamic coating. A number of coatings, both static and dynamic ones, were introduced into capillary electrophoresis (J. Horvath and V. Dolnik, Wall coatings in capillary electrophoresis. Electrophoresis, 22 (2001) 644-655). Low values of electroosmotic mobility can be measured by the Williams-Vigh method (B. A. Williams and G. Vigh, Determination of accurate electroosmotic mobility and analyte effective mobility values in the presence of charged interacting agents in capillary electrophoresis. Anal. Chem. 69 (1997) 4445-4451).

To remove analytes and other compounds adsorbed on the capillary wall, the capillary is typically washed with 0.1 M N NaOH. Nevertheless, a flush with a high-pH NaOH solution results in formation of a liquid sodium silicate layer on the inner fused silica capillary surface (K. Klepárnik Z. Malá, P. Baček, Fast separation of DNA sequencing fragments in highly alkaline solutions of linear polyacrylamide using electrophoresis in bare silica capillaries. Electrophoresis. 2001, 22, 783-788). This liquid layer prevents any wall interactions. Therefore, the capillary has to flushed with an acidic solution to neutralize the liquid sodium silicate at the capillary surface. Typically, 0.1 M HCl is used to for this purpose.

Biopolymers are frequently denatured prior the CE separation. DNA is usually denatured with urea, formamide, methyl formamide, dimethyl formamide, ethyl formamide, and dimethyl sulfoxide. Proteins can be denatured with sodium dodecyl sulfate, lithium dodecyl sulfate, sodium lauroyl sarcosinate, sodium decyl sulfate, lauric acid, urea, thiourea, formamide, methyl formamide, dimethyl formamide, ethyl formamide, dimethyl sulfoxide.

Analytes separated by capillary electrophoresis can be detected online by various detection techniques. UV absorption and laser-induced fluorescence of fluorescently labeled analytes are the most frequently used detection techniques in capillary electrophoresis.

Dynamic Coatings to Suppress Electroosmotic Flow

Chiari (U.S. Pat. No. 6,410,668) disclosed copolymers of various derivatives of acrylamide and methacrylamide with various glycidyl group containing monomers to form a highly hydrophilic, dynamic coating that suppresses electroosmotic flow.

Madabhushi et al. (U.S. Pat. No. 5,567,292) disclosed copolymers uncharged water-soluble silica-adsorbing polymers for suppressing electroendoosmotic flow, selected from the group consisting of polylactams, such as polyvinylpyrrolidone; N,N-disubstituted polyacrylamides; and N-substituted polyacrylamides.

Borate Polymorphs and Borosilicate Glass

Borates form various structures depending on pH. Borates are incorporated in a structure with silica to form borosilicate glass (A. K. Varshneya, Fundamentals of Inorganic Glasses, Academic Press, Boston 1994).

Polyol Borate Complexes (For the sake of simplification, we call polyol any compound that contains at least 2 hydroxyl groups in its molecule.)

M. van Duin et al. (M. van Duin, J. A. Peters, A. P. G. Kieboom and H. van Beldam, Studies on borate esters I. The pH dependence of the stability of esters of boric acid and borate in aqueous medium as studied by $^{11}$B NMR. Tetrahedron 40 (1984) 2901-29141) described esters generated between boric acid and glycol, glycolic acid, oxalic acid, and glyceric acid.

Taylor et al. (M. J. Taylor, J. A. Grigg anf I. H. Laban, Triol borates and aminoalcohol derivatives of boric acid: Their formation and hydrolysis. Polyhedron 15 (1996) 3261-3270) described formation of mono-chelates, bis-chelates and cage structure between borates and triols, specifically Tris, tris (hydroxymethyl)ethane, tris(hydroxymethyl)propane, and triethanolamine.

Sonoda et al. (A. Sonoda, N. Takagi, K. Ooi, T. Hirotsu, Complex formation between boric acid and triethanolamine in aqueous solutions. Bull. Chem. Soc. Jpn 71 (1998) 161-166) described formation of triethanolamine-borate complexes in aqueous solutions.

Yan et al. (J. Yan, G. Springsteen, S. Deeter, B. Wang, The relationship among $pK_a$, pH, and binding constants in the interaction between boronic acids and diols- it is not as simple as it appears. Tetrahedron 60 (2004) 11205-11209) described the relationship between $pK_a$ of monosubstituted boronic acids and their substituents using a Hammett plot.

pH Gradients by Polyols and Borate Buffers

Troitsky et al. (G. V. Troitsky, V. P. Zav'yalov, I. F. Kirjukhin, V. M. Abramov and G. Ju. Agitsky, Isoelectric focusing of proteins using a pH gradient created by a concentration gradient of nonelectrolytes in solution. Biochim. Biophys. Acta 400 (1975) 24-31) developed a new method of generating pH gradient by generating a concentration gradient of polyols in the presence of boric acid.

Shukun et al. (S. A. Shukun, A. V. Gavryushkin, V. N. Brezgunov, and V. P, Zav'yalov, Protein separation in pH gradients using free-flow electrophoretic apparatus. II. The pH gradients formed by the concentration gradient of boric acid in solutions of borax and mannitol. Electrophoresis 6 (1985) 75-77) generated pH gradient 3.5 to 9.2 for free-flow electrophoresis by forming a concentration gradient of boric acid in solutions of borax and mannitol for protein separation by free-flow electrophoresis.

Murel (U.S. Pat. No. 4,925,545) disclosed a method for forming pH gradients for use in electrophoresis and isoelectric focusing. The method generates a concentration gradient of polyols that interact with boric acid, borax, and/or other borate constituents and form acidic complexes with the anchored polyhydroxyl groups, generating pH gradient.

Borate Buffer for Electrophoresis of Carbohydrates and Polyols

Honda et al. (S. Honda, S. Suzuki, A. Nose, K. Yamamoto and K. Kakehi, Capillary zone electrophoresis of reducing mono- and oligo-saccharides as the borate complexes of their 3-methyl-1-phenyl-2-pyrazolin-5-one derivatives. Carbohydrate Res. 215 (1991) 193-198) separated derivatized aldopentoses and aldohexoses by CE in 100 mM borate buffer, pH 9.5.

Hoffstetter et al. (S. Hoffstetter-Kuhn, A. Paulus, E. Gassmann, and H. M. Widmer, Influence of borate complexation on the electrophoretic behavior of carbohydrates in capillary electrophoresis. Anal. Chem. 63 (1991) 1541-1547) disclosed the use of borate complexation for improving separation of carbohydrates in CE.

Stefansson and Novotny (M. Stefansson, M. Novotny: Separation of Complex Oligosaccharide Mixtures by Capillary Electrophoresis in the Open-Tubular Format Anal. Chem., 1994, 66, 1134-1140) described the use of borate buffer for separation of polysaccharides.

Landers et al. (J. P. Landers, R. P. Oda, M. D. Schuchard, Separation of boron-complexed diol compounds using high-performance capillary electrophoresis. Anal. Chem., 64 (1992) 2846-2851) separated diols with borate as counter ion.

Plocek and Chmelik (J. Plocek. and J. Chmelik, Separation of disaccharides as their borate complexes by capillary electrophoresis with indirect detection in visible range. Electrophoresis 18 (1997) 1148-1152) separated disaccharides by CE with indirect detection, when the concentration sensitivity for sucrose was 2 mM in 200 mM borate.

Quirino and Terabe J. P. Quirino and S. Terabe, Sweeping of neutral analytes via complexation with borate in capillary zone electrophoresis Chromatographia 53 (2001) 285-289) concentrated monosaccharides, catechols, and nucleosides by sweeping these analytes with borate.

Tris Borate Buffer for Electrophoresis of Glycoproteins

Weitzman et al. (S. Weitzman, V. Scott and K. Keegstra, Analysis of glycopeptides as borate complexes by polyacrylamide gel electrophoresis. Anal. Biochem. 97 (1979) 438-449) developed a new method of polyacrylamide gel electrophoresis in a Tris-borate buffer to analyze glycopeptides. The resolution of glycopeptides depended on the inclusion of borate ions in the sample, the gel, and the electrophoresis buffer. The borate ions reacted with neutral sugars, converting them into charged complexes which migrated during electrophoresis.

Keo et al. (U.S. Pat. No. 5,599,433) disclosed a buffer for capillary electrophoresis of glycosylated proteins comprising sodium borate and 3-cyclohexylamino-1-propanesulfonic acid.

Tris Borate Buffer for Electrophoresis of Nucleic Acid

Peacock and Dingman (A. C. Peacock, C. W. Dingman, Resolution of Multiple Ribonucleic Acid Species by Polyacrylamide Gel Electrophoresis. Biochemistry 6 (1967) 1818-1827) described electrophoresis of ribonucleic acid in polyacrylamide gels and resolution of multiple RNA species by polyacrylamide gel electrophoresis with Tris borate EDTA and boric acid buffers for electrophoresis in samples without glycerol.

Fuller (U.S. Pat. Nos. 5,314,595, 5,830,642, and 5,849,166) disclosed a method and a separation medium for capillary electrophoresis of DNA fragments containing glycerol, dithiothreitol (DTT) and trehalose or other sugars gel in the presence of a buffer lacking boric acid.

Carninci et al. (P. Carninci, S. Gustincich, S. Bottega, C. Patrosso; G. Del Sal, G. Manfioletti, C. Schneider, A simple discontinuous buffer system for increased resolution and speed in gel electrophoretic analysis of DNA sequence. Nucleic Acid Res. 18 (1990) 204-208) described a standard sequencing gel system using Tris/Borate/EDTA buffer (TBE). They also described a discontinuous buffer system using Tris-sulphate and Tris-borate. The Tris-sulphate was used as a running gel buffer, and Tris-borate as a tank buffer.

Strege and Lagu (M. Strege and A. Lagu, Separation of DNA restriction fragments by capillary electrophoresis using coated fused silica capillaries. Anal. Chem. 63 (1991) 1233-1236.) separated DNA restriction fragments in coated capillary in 0.5% methylcellulose, 50 mM Tris-borate, pH 8.0.

Brumley and Smith (R. L. Brumley and L. M. Smith, Rapid DNA sequencing by horizontal ultrathin gel electrophoresis. Nucl. Acids Res. 19 (1991) 4121-4126) describe the use of a borate buffer for a sequencing gel.

Bashkin et al. (J. Bashkin, M. Marsh, D. Barker, R. Johnston, DNA sequencing by capillary electrophoresis with a hydroxyethylcellulose sieving buffer. Appl. Theor. Electrophor. 6 (1996) 23-28) used TBE buffer containing 89 mM Tris, 89 mM boric acid, 1 mM EDTA with HEC to separate DNA sequencing fragments in a coated capillary.

Schwinefus and Bloomfield (J. J. Schwinefus, V. A. Bloomfield, The greater negative charge density of DNA in Tris-borate buffers does not enhance DNA condensation by multivalent cations. Biopolymers 54 (2000) 572-577) described the effect of Tris borate on the binding of multivalent cations to DNA.

Stellwagen et al. (N. C. Stellwagen, C. Gelfi and P. G. Righetti, DNA and buffers: the hidden danger of complex formation. Biopolymers 54 (2000) 137-142) described formation of borate-DNA complexes in polyacrylamide gels. They did not observe them in agarose gel due to the competition of agarose fibers for the borate residues.

Righetti et al. (P. G. Righetti, C. Gelfi and M. R. d'Acunto, Recent progress in DNA analysis by capillary electrophoresis. Electrophoresis 23 (2002) 1361-1374) studied interactions of DNA and small ions particularly borates. They were not able to answer the question, whether or not borate ions would bind to DNA.

Brody and Kern (J. R. Brody and S. E. Kern, Sodium boric acid: a Tris-free, cooler conductive medium for DNA electrophoresis, BioTechniques 36 (2004) 214-216) concluded sodium borate is a better buffer than Tris borate for slab gel electrophoresis of DNA.

Buchmueller and Weeks (K. L. Buchmueller and K. M. Weeks, Tris-borate is a poor counterion for RNA: a cautionary tale for RNA folding studies. Nucleic Acid Res. 32 (2004) e184) described difficulties related to the use of Tris borate buffer for electrophoresis of RNA.

Karger et al. (U.S. patent application 20040222095) disclosed the use of dimethyl sulfoxide for denaturation of DNA in capillary electrophoresis.

Singhal et al. (H. Singhal, Y. R. Ren and S. E. Kern, Improved DNA Electrophoresis in conditions favoring polyborates and Lewis acid complexation. PLOS one 5 (2010) e11318) proposed formation of polyborates and their complex formation with DNA.

Tris Borate Buffer for SDS Electrophoresis

Poduslo (J. F. Poduslo, Glycoprotein molecular-weight estimation using sodium dodecyl sulfate-pore gradient electrophoresis: Comparison of Tris-glycine and Tris-borate-EDTA buffer systems. Anal. Biochem. 114 (1981) 131-139) compared the accuracy of molecular-weight estimates for glycoproteins by SDS pore gradient electrophoresis in a Tris-glycine buffer system and Tris-borate-EDTA buffer and found the latter more accurate.

Wu and Regnier (D. Wu and F. E. Regnier, Sodium dodecyl sulfate-capillary gel electrophoresis of proteins using non-cross-linked polyacrylamide, J. Chromatogr. A, 608 (1992) 349-356) separated proteins by SDS CSE in bare capillaries with linear polyacrylamide as a sieving polymer. They prepared their protein samples in 100 mM Tris 250 mM borate with SDS, but did not disclose the composition of the sieving medium.

Zhang et al. (Y. Zhang, H. K. Lee and Sam F. Y. Li, Separation of myoglobin molecular mass markers using non-gel sieving capillary electrophoresis. J. Chromatogr. A 744 (1996) 249-257) described SDS capillary electrophoresis in bare capillaries using 12% dextran, 0.4 M Tris borate, 0.1% SDS, and 10% glycerol.

Harvey et al. (M. D. Harvey, D. Bandilla and P. R. Banks, Subnanomolar detection limit for sodium dodecyl sulfate—capillary gel electrophoresis using a fluorogenic non covalent dye. Electrophoresis 19 (1998) 2169-2174) performed SDS capillary electrophoresis in separation medium containing 8% linear polyacrylamide, 0.1 M Tris, 0.25 M borate, pH 8, and 0.05% SDS.

Bean and Lockhart (S. R. Bean and G. L. Lockhart, Sodium dodecyl sulfate capillary electrophoresis of wheat proteins. 1. Uncoated capillaries J. Agric. Food Chem. 47 (1999) 4246-4255) found optimum composition for SDS capillary electrophoresis in bare capillaries 10% dextran, 400 mM or 600 mM Tris borate buffer (pH=8.5), 0.1% SDS, and 10% ethylene glycol.

Liu et al. (U.S. patent applications 20040050702 and 20090314638) disclosed a sieving medium for SDS capillary electrophoresis of proteins comprising about 10% dextran, 600 mM Tris borate, 2 g/L SDS, 1 mM EDTA and 10% glycerol.

Other Electrophoretic Separations in Borate Buffer

Chen (F. T. A. Chen, Rapid protein analysis by capillary electrophoresis. J. Chromatogr. A 559 (1991) 445-453) separated serum proteins in 100 mM borate buffer pH 11.5 and 150 mM borate buffer, pH 10.5.

Alter and Kim (U.S. Pat. No. 5,753,094) disclosed a sample diluent for capillary electrophoresis based on a borate buffer.

Smith (U.S. Pat. No. 5,212,299) disclosed a composition for electrophoresis comprising glyceryl agarose and 20-400 mM borate.

Lee et al. (U.S. patent application 20090166200) disclosed a high-salt borate-buffered agarose gel for identification of a candidate vaccine.

BRIEF SUMMARY OF THE INVENTION

The present invention is suitable for electrophoresis in bare fused silica capillaries and on bare chips suppressing electroosmotic flow and improving separation. Disclosed is the separation medium containing borate buffers, alcohols and polyols and method of its use.

DETAILED DESCRIPTION OF THE INVENTION

Figure 1:
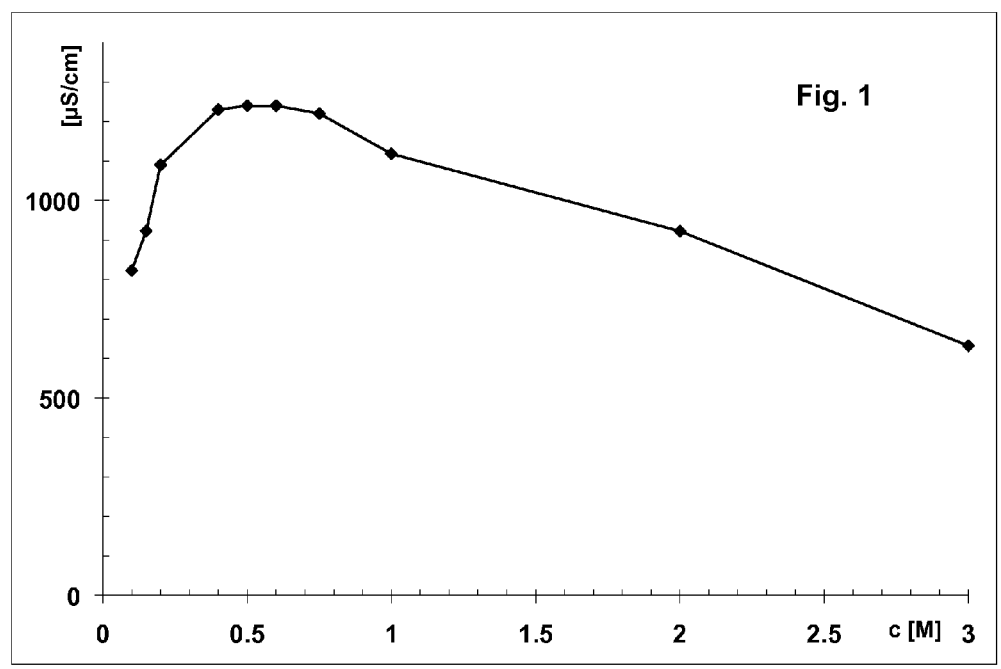
FIG. 1 shows the concentration dependence of conductivity of equimolar Tris borate solutions.

We propose a composition of a separation medium for electrophoresis in bare channel formed either as a fused silica capillary or a microchip. We disclose here a composition for sample preparation of proteins prior their electrophoretic size separation, consisting of:
a) a neutral hydrophilic polymer at the concentration from about 0 g/L to about 200 g/L;
b) a neutral polyol at the concentration from about 20 g/L to about 200 g/L;
c) a biopolymer denaturant at the concentration from about 0 g/L to about 420 g/L;
d) a counter ion at the concentration between about 0.02 M and about 3 M;
e) boric acid at the concentration from about 0.1 M and about 3 M, with the proviso that
1) if said biopolymer denaturant is SDS and said counter ion is Tris the concentration of boric acid is in the range from about 0.8 M to about 3 M;
2) if said counter ion is sodium the concentration of boric acid is in the range from about 0.8 M to about 3 M.

We also disclose a separation medium for capillary sieving electrophoresis, wherein said neutral hydrophilic polymer is selected from the group of polymers consisting of hydroxyethyl cellulose, hydroxypropyl cellulose, hydroxyisopropyl cellulose, locust bean gum, tara gum, guar gum, hydroxyisopropyl guaran, fenugreek gum, konjac, pullulan, pustulan, agarose, laminaran, dextran, amylose, schyzophyllan, nigeran, poly(vinyl alcohol), poly(vinyl pyrrolidone), poly(ethylene oxide), poly(dimethyl acrylamide), and polyacrylamide.

Further we disclose a separation medium for capillary electrophoresis, wherein said biopolymer denaturants are selected from the group of denaturants consisting of urea, thiourea, formamide, methyl formamide, dimethyl formamide, ethyl formamide, dimethyl sulfoxide sodium dodecyl sulfate, lithium dodecyl sulfate, sodium lauroyl sarcosinate, sodium decyl sulfate, and lauric acid.

We also disclose a separation medium for capillary electrophoresis, wherein said neutral polyol is selected from the group of polyols consisting of glycerol, ethylene glycol, mannitol, sorbitol, glucitol, and dextrin.

Further we disclose a separation medium for capillary electrophoresis, wherein said counter ion is selected from the group of bases consisting of lithium, sodium, arginine, lysine, histidine, imidazole, methylimidazole, morpholine, ethylmorpholine, tris(hydroxymethyl)aminomethane, tris(hydroxymethyl)ethane, tris(hydroxymethyl)propane, bis-(2-hydroxyethyl)-amino-tris(hydroxymethyl)-methane (Bis-Tris), 1,3-bis[tris(hydroxymethyl)methylamino]propane (Bis-Tris Propane), 2-amino-2-methylpropane-1,3-diol (Ammediol), ethanolamine, diethanolamine, triethanolamine, triisopropanolamine, N-methylglucamine, glucosamine, galactosamine, and fructosamine.

We also disclose a separation medium for capillary electrophoresis, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is from about 0.1 M to about 0.5 M triethanolamine and boric acid is present at the concentration of from about 0.4 M to about 1 M.

Further we disclose a separation medium for capillary electrophoresis, wherein said neutral hydrophilic polymer is from about 5 g/L to about 60 g/L polyacrylamide, said biopolymer denaturant is from about 0.1 M to about 2 M dimethyl sulfoxide, said counter ion is from about 0.1 M to about 0.5 M triethanolamine and boric acid is present at the concentration of from about 0.4 M to about 1 M.

We also disclose a separation medium for capillary electrophoresis, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is Tris and boric acid is present at the concentration of about 1 M.

Further we disclose a separation medium for capillary electrophoresis, wherein said neutral hydrophilic polymer is from about 5 g/L to about 60 g/L polyacrylamide, said biopolymer denaturant is from about 0.1 M to about 2 M dimethyl sulfoxide, said counter ion is Tris and boric acid is present at the concentration of about 1 M.

We also disclose a separation medium for capillary electrophoresis, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is about 0.1 M Bis-Tris Propane, and boric acid is present at the concentration of about 1 M.

Further we disclose a separation medium for capillary electrophoresis, wherein said neutral hydrophilic polymer is from about 5 g/L to about 60 g/L hydroxyethyl cellulose, said biopolymer denaturant is from about 0.1 M to about 2 M dimethyl sulfoxide, said neutral polyol is from about 20 g/L to 200 g/L mannitol, said counter ion is about 0.1 M Bis-Tris Propane, and boric acid is present at the concentration of about 1 M.

We also disclose a separation medium for capillary electrophoresis, wherein said neutral hydrophilic polymer is from about 5 g/L to about 60 g/L hydroxyethyl cellulose, said biopolymer denaturant is from about 0.1 M to about 2 M dimethyl sulfoxide, said neutral polyol is from about 20 g/L to 200 g/L glycerol, said counter ion is about 0.1 M Bis-Tris Propane, and boric acid is present at the concentration of about 1 M.

Further we disclose a separation medium for capillary electrophoresis, wherein said neutral hydrophilic polymer is about 16 g/L hydroxyethyl cellulose, said biopolymer denaturant is about 0.8 M dimethyl sulfoxide, said neutral polyol is about 100 g/L mannitol, said counter ion is about 0.3 M Bis-Tris Propane, and boric acid is present at the concentration of about 0.3 M.

We also disclose a separation medium for capillary electrophoresis, wherein said neutral hydrophilic polymer is about 16 g/L hydroxyethyl cellulose, said biopolymer denaturant is about 0.8 M dimethyl sulfoxide, said neutral polyol is about 0.5 M sorbitol, said counter ion is about 0.4 M Bis-Tris Propane, and boric acid is present at the concentration of about 0.2 M.

Further we disclose a separation medium for capillary electrophoresis of Claim 1, wherein said neutral hydrophilic polymer is about 16 g/L hydroxyethyl cellulose, said biopolymer denaturant is about 0.8 M dimethyl sulfoxide, said neutral polyol is about 0.5 M sorbitol, said counter ion is about 0.4 M Tris, and boric acid is present at the concentration of about 0.4 M.

We also disclose a separation medium for capillary electrophoresis of Claim 1, wherein said counter ion is about 0.2 M Bis-Tris Propane, and boric acid is present at the concentration of about 0.4 M.

We also disclose a separation medium for capillary electrophoresis, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is from about 0.1 M to about 0.6 M Bis-Tris Propane, and boric acid is present at the concentration from about 0.2 M to about 1 M.

Further we disclose a separation medium for capillary electrophoresis, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L mannitol, said counter ion is from about 0.1 M to about 0.6 M Bis-Tris Propane, and boric acid is present at the concentration from about 0.2 M to about 1 M.

We also disclose a separation medium for capillary electrophoresis, wherein said neutral hydrophilic polymer is about 100 g/L dextran ($M_w$ $2 \times 10^6$), said biopolymer denaturant is about 2 g/L sodium dodecyl sulfate, said neutral polyol is about 100 g/L mannitol, said counter ion is about 0.3 M Bis-Tris Propane, and boric acid is present at the concentration of about 0.3 M.

Further we disclose a separation medium for capillary electrophoresis, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is about 0.3 M Tris, and boric acid is present at the concentration of about 1.2 M.

We also disclose a separation medium for capillary electrophoresis, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is from about 0.2 M to about 0.6 M triethanolamine, and boric acid is present at the concentration from about 0.2 M to about 0.6 M.

Further we disclose a separation medium for capillary electrophoresis, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L mannitol, said counter ion is from about 0.2 M to about 0.6 M triethanolamine, and boric acid is present at the concentration from about 0.2 M to about 0.6 M.

We also disclose a procedure for capillary electrophoresis performed in a separation channel, said separation channel made in an insulating body, said insulating body selected from the group consisting of fused silica capillary, fused silica chip, silicon chip, glass chip, poly(methyl methacrylate) chip, polycarbonate chip, and cyclic polyolefin chip, wherein said procedure comprises following steps:
flushing said separation channel with about 0.1 M HCl;
filling said separation channel with said separation medium for capillary electrophoresis of Claim 1;
injecting a sample into said separation channel;
separating components of said sample by applying electric voltage; and
detecting said separated components of said sample online.

EXAMPLES

The separations described in these examples were performed in a prototype instrument for capillary electrophoresis with LIF detection at 488 nm/530 nm at room temperature in bare capillaries of internal diameter 75 μm and outer diameter 360 μm and in 3D CE instrument (Agilent) with UV detection at 214 nm.

Example 1

Effect of the Concentration of Tris(Hydroxymethyl)Aminomethane (Tris)Borate on its Conductivity Conductivity of salts typically grows with their concentration. As documented in FIG. 1, conductivity of Tris borate solution increases with concentration only to a certain level. At higher concentration, conductivity starts to diminish. This can be simply explained by complexation of borate with Tris. It not only reduces $pK_a$ of borate as neutral polyols do, but also neutral cage complexes are formed at high concentration. Other salts of polyol bases with boric acid behave in a similar way.

Example 2

Figure 2:
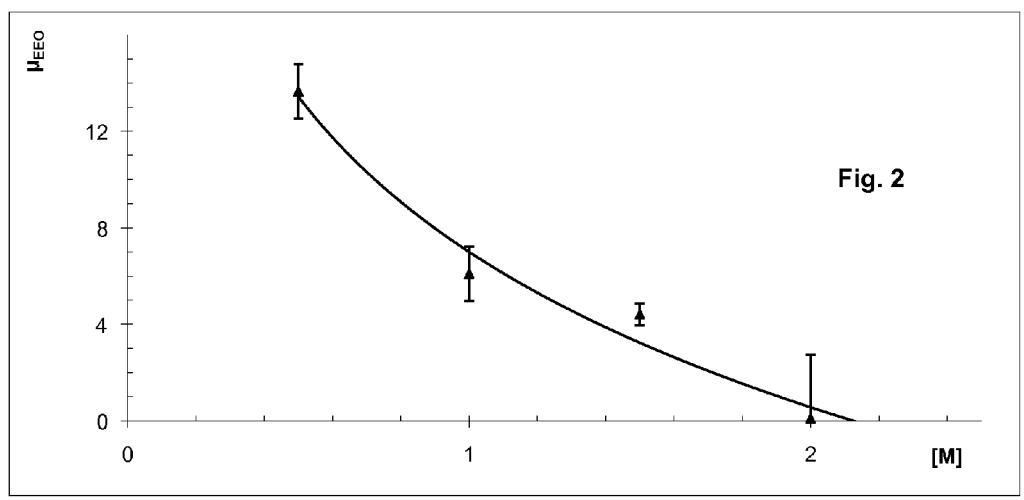
FIG. 2 demonstrates the concentration dependence of electroosmotic mobility of bare fused silica capillary in equimolar Tris borate solutions. (Electroosmotic mobilities $\mu_{EEO}$ expressed in $10^{-9}$ $m^2V^{-1}s^{-1}$.)

Suppression of Electroosmotic Mobility in Bare Fused Silica Capillary by Borates Borates seem to easily bind silica surfaces generating a monolayer, which we conjecture to be structurally similar to borosilicate glass. Because boric acid has higher $pK_a$ than silanol groups of silica, electroosmotic flow in fused silica capillaries (or more exactly electroosmotic mobility $\mu_{EEO}$) decreases with increasing concentration of borate. Simple addition of boric acid, however, reduces pH and that is detrimental to DNA CE separation and protein separation by SDS CSE. To keep pH of the background electrolyte (BGE) at a favorable pH range about 7-9, polyol counter ions with $pK_a$ in this range, such as Tris, Bis-Tris, Bis-Tris Propane, triethanolamine, etc., are preferred to neutralize boric acid. Complex formation reduces conductivity of BGE and allows high voltages to be applied, substantially reducing analysis time. What is even more important is the polyol base-borate complexes still bind capillary silica surfaces and suppress ζ-potential and electroosmotic mobility. As the concentration of borate increases, the electroosmotic mobility decreases. This was demonstrated for Tris borate BGE when the electroosmotic mobility was measured by Williams-Vigh method (FIG. 2).

Figure 3:
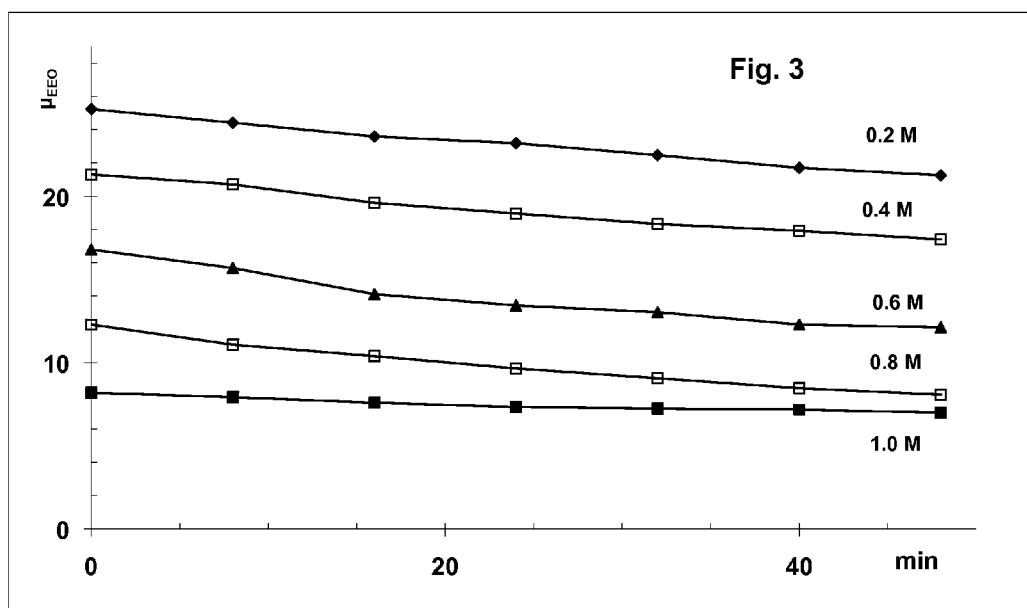
FIG. 3 demonstrates the time course of the electroosmotic mobility and the effect of borate concentration on the electroosmotic mobility in bare fused silica capillary and 100 mM triethanolamine, 0.2-1.0 M boric acid. (Electroosmotic mobilities $\mu_{EEO}$ expressed in $10^{-9}$ $m^2V^{-1}s^{-1}$.)

The polyol counter ion need not be necessarily equimolar with borate to suppress electroosmotic mobility. As shown in FIG. 3, the electroosmotic mobility was more suppressed when the concentration ratio borate/triethanolamine increased. FIG. 3 also suggests the kinetics of the electroosmotic suppression: at lower borate/triethanolamine concentration ratio, the equilibration of electroosmosis was slower than at high concentration ratio.

Figure 4:
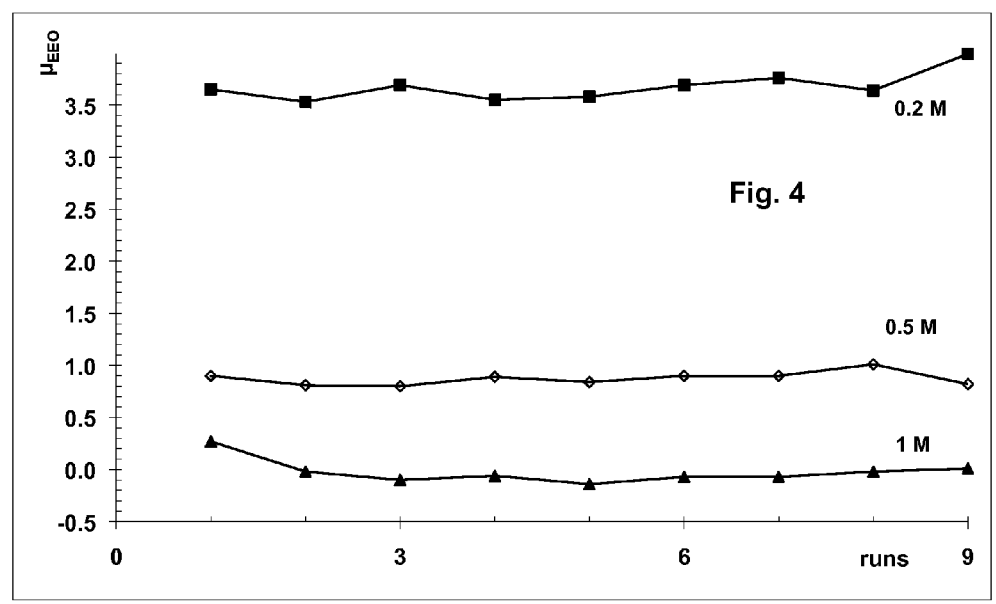
FIG. 4 demonstrates the concentration effect of 0.2-1.0 M 1Bis-Tris Propane borate, 100 g/L mannitol, on the electroosmotic mobility in bare fused silica capillary. (Electroosmotic mobilities $\mu_{EEO}$ expressed in $10^{-9}$ $m^2V^{-1}s^{-1}$.)

Bis-Tris Propane, containing 6 hydroxyl groups and 2 ionizable amino groups in its molecule, strongly interacts with boric acid. In the presence of 100 g/L mannitol, which also competed for boric acid to generate complexes with, the increasing concentration of equimolar Bis-Tris Propane borate reduced electroosmotic mobility and eventually reversed its sign as demonstrated in FIG. 4. The electroosmotic mobility was also quickly equilibrated.

Example 3

Figure 5:
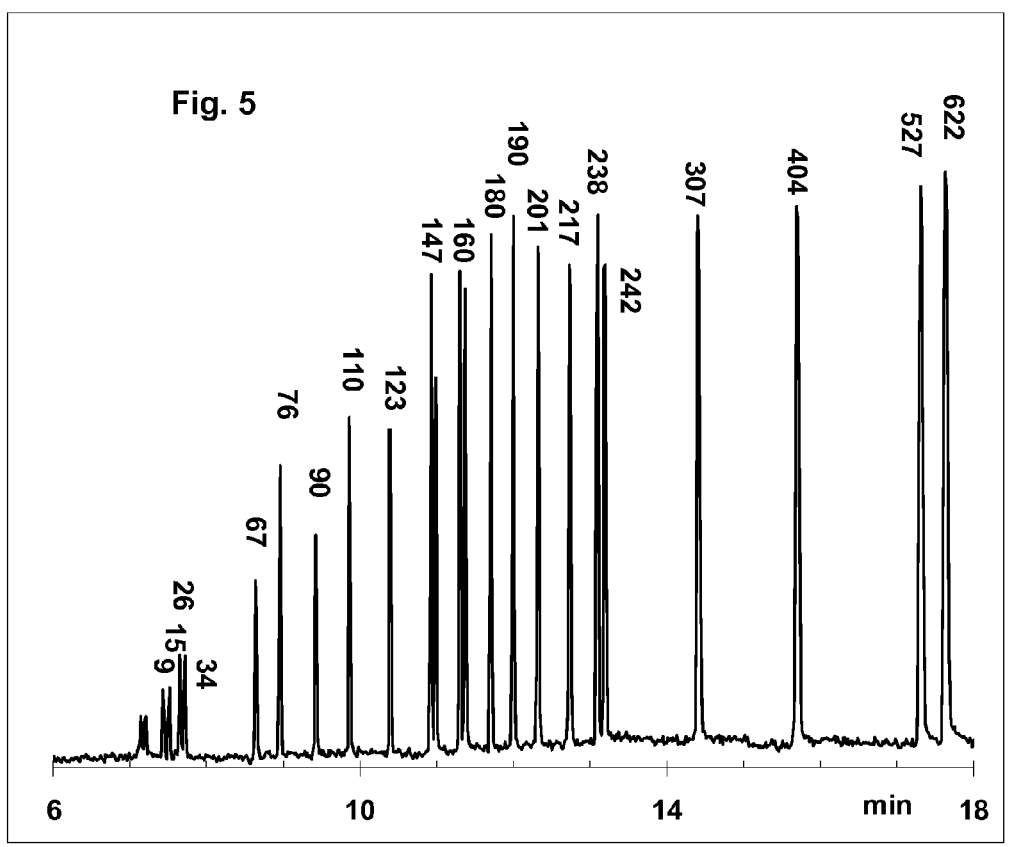
FIG. 5 shows a separation of pBR322 MspI restriction fragments in triethanolamine borate buffer. Separation medium: 12 g/L HEC, 0.8 M DMSO, 100 mM triethanolamine, 400 mM boric acid, 1×SYBR Green II. Bare capillary, total length=40 mm, effective length=20 mm, ID=75 µm, OD=360 µm. Voltage: −8 kV. LIF detection: 488 nm excitation, 530 nm emission. Electrokinetic injection: 1 s at −8 kV. Sample: pBR322 MspI restriction fragments in 10 mM Tris-HCl, pH 8.0 (New England BioLabs, Inc.) diluted 10× with 0.1 M Tris, HEPES.
Figure 6:
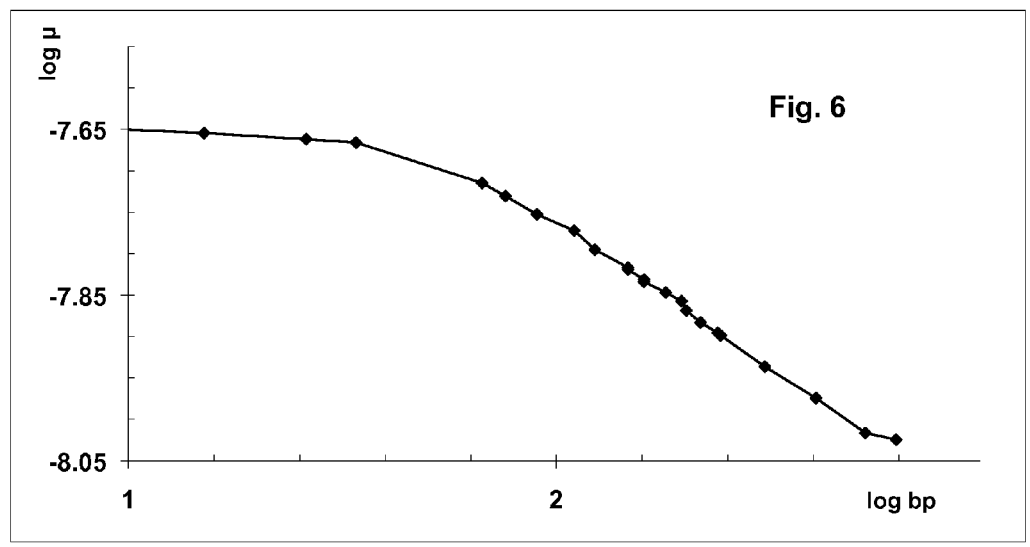
FIG. 6 shows a log-log mobility curve of DNA restriction fragments separated in triethanolamine borate buffer. For the separation conditions, see FIG. 5.

Electrophoretic Separation of DNA Fragments in HEC with Triethanolamine Borate Buffer Triethanolamine borate as BGE suppressed electroosmotic flow and improved resolution of DNA separation by capillary sieving electrophoresis (FIG. 5). pBR322 MspI restriction fragments were fully separated in a bare capillary filled with 12 g/L hydroxyethyl cellulose (HEC), 0.8 M DMSO, 100 mM triethanolamine, 400 mM boric acid, and 1×SYBR Green II. The sample contained 2 fragments with 147 base pairs and 2 fragments having 160 base pairs. As it is shown in FIG. 5, capillary electrophoresis in the proposed separation medium separated these fragments with a baseline resolution. Whereas BGE containing 100 mM triethanolamine and 400 mM boric acid did not completely eliminate electroosmotic flow (FIG. 3), the presence of HEC helped to suppress electroosmotic flow even further by increasing viscosity of the solution. Log-log mobility plot of the separated restriction fragments confirmed the majority of separated DNA fragments migrated in the reputation mode (FIG. 6).

Figure 7:
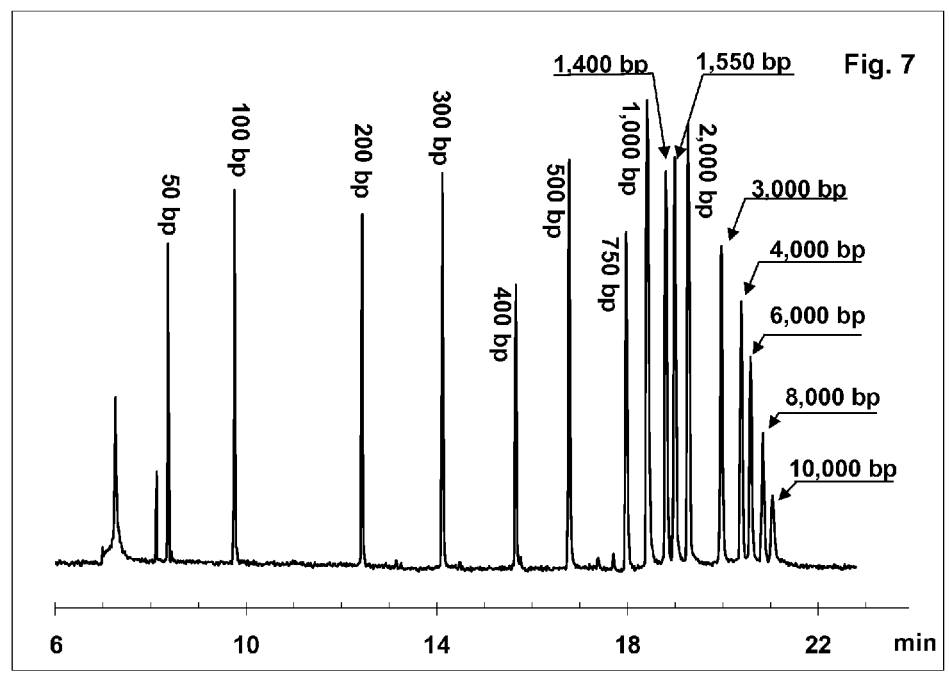
FIG. 7 shows a separation of HiLo™ DNA in triethanolamine borate buffer. Separation medium: 12 g/L HEC, 0.8 M DMSO, 100 mM triethanolamine, 400 mM boric acid, 1×SYBR Green II. Bare capillary, total length=40 mm, effective length=20 mm, ID=75 µm, OD=360 µm. Voltage: −8 kV. LIF detection: 488 nm excitation, 530 nm emission. Electrokinetic injection: 5 s at −8 kV. Sample: HiLo™ (Minnesota Molecular, Inc.).
Figure 8:
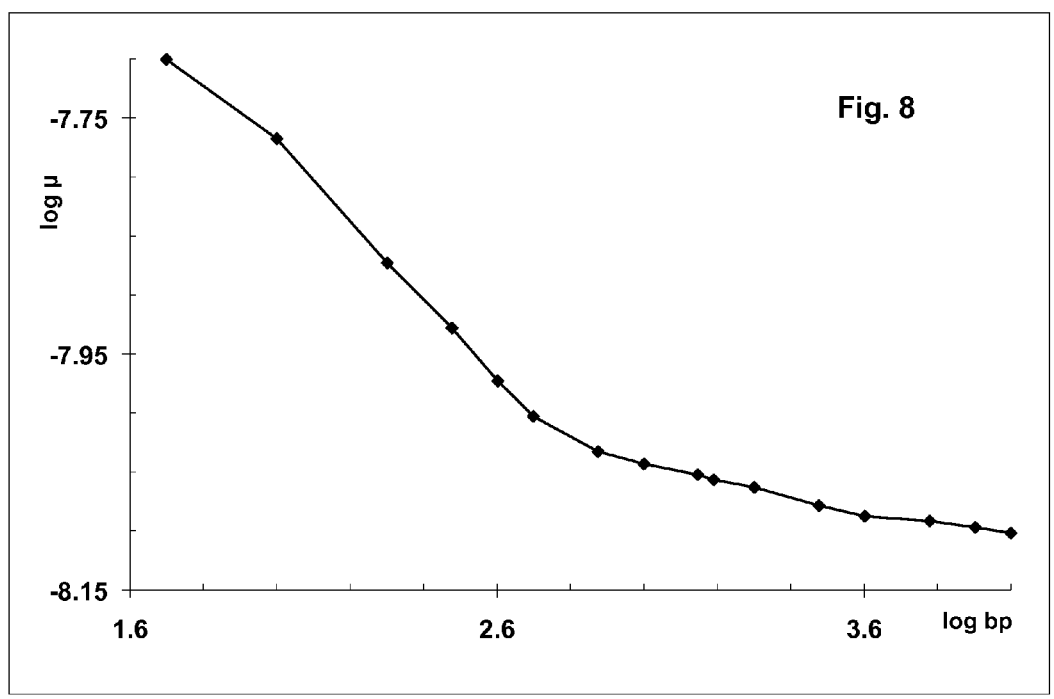
FIG. 8 shows a log-log mobility curve of HiLo™ DNA separated in triethanolamine borate buffer. For the separation conditions, see FIG. 7.

Triethanolamine borate buffer was also used to separate HiLo™, a mixture of 16 DNA fragments having 50-10,000 base pairs. As it is shown in FIG. 7, all DNA fragments were separated with a baseline resolution. Log-log mobility curve for this separation is shown in FIG. 8.

Example 4

Figure 9:
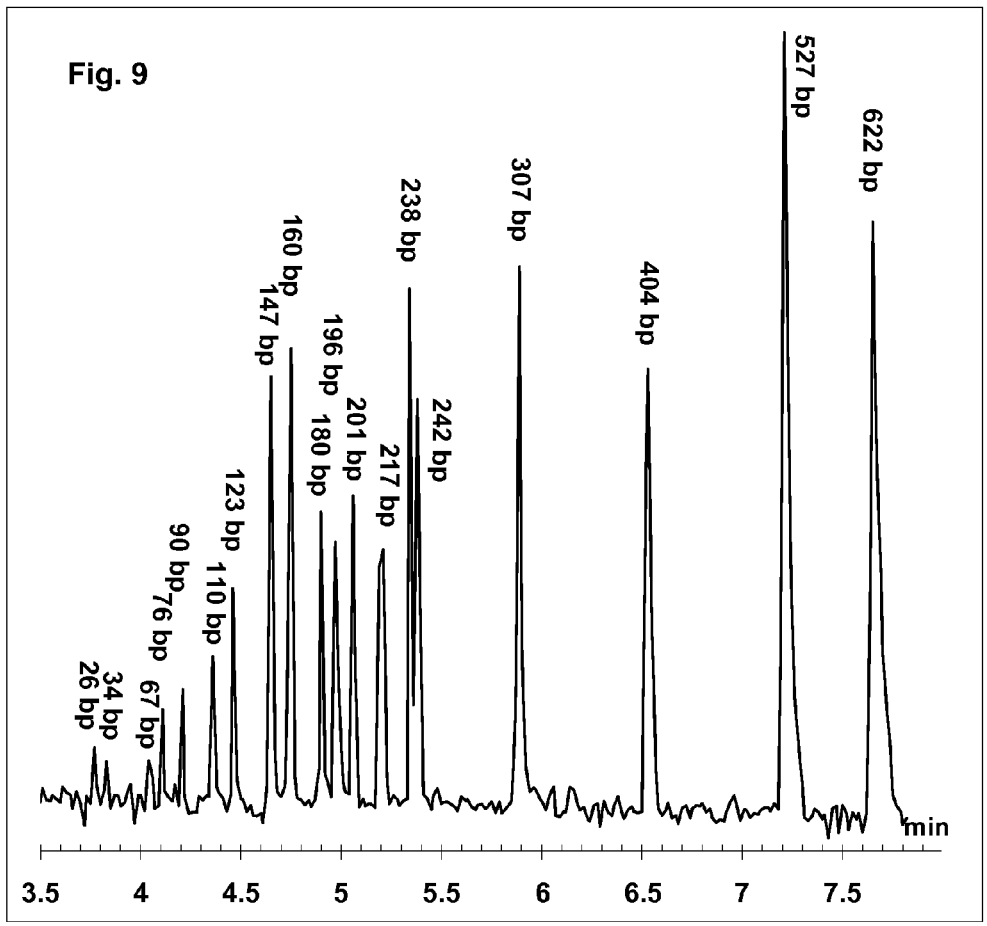
FIG. 9 shows a separation of pBR322 MspI restriction fragments on glass microchip in 20 g/L LPA and Tris borate buffer. Separation medium: 20 g/L LPA ($M_w$ 7.0 M), 0.8 M DMSO, 100 mM Tris, 1.0 mM boric acid. Bare glass microchip: TT-100 (Micralyne, Inc.) Separation voltage: −2 kV (waste and sample electrode voltage: −180 V). LIF detection: 488 nm excitation, 530 nm emission. Electrokinetic injection: 60 s at −150 V. Sample: 10 µL pBR322 MspI restriction fragments in 10 mM Tris-HCl, pH 8.0 (New England BioLabs, Inc.), 3 µL 5×SYBR Green II in DMSO.

Electrophoretic Separation of DNA Fragments in Linear Polyacrylamide with Tris Borate Buffer in a Glass Chip Separation of pBR322 MspI restriction fragments in linear polyacrylamide (LPA) with Tris borate on a glass chip is shown in FIG. 9. (Separation medium: 20 g/L LPA ($M_w$ 7.0 M), 0.8 M DMSO, 100 mM Tris, 1.0 mM boric acid.) LPA is a polymer with excellent sieving properties but insufficient suppression of electroosmotic flow. Here, the Tris borate buffer enabled a quick separation of most of the DNA fragments. The pairs of 147 base pairs as well as 160 base pairs remained unseparated and fragments 238 bp and 242 bp were only partly separated. In the separation channel having the effective length 80 mm, the separation was completed in less than 8 min.

Figure 10:
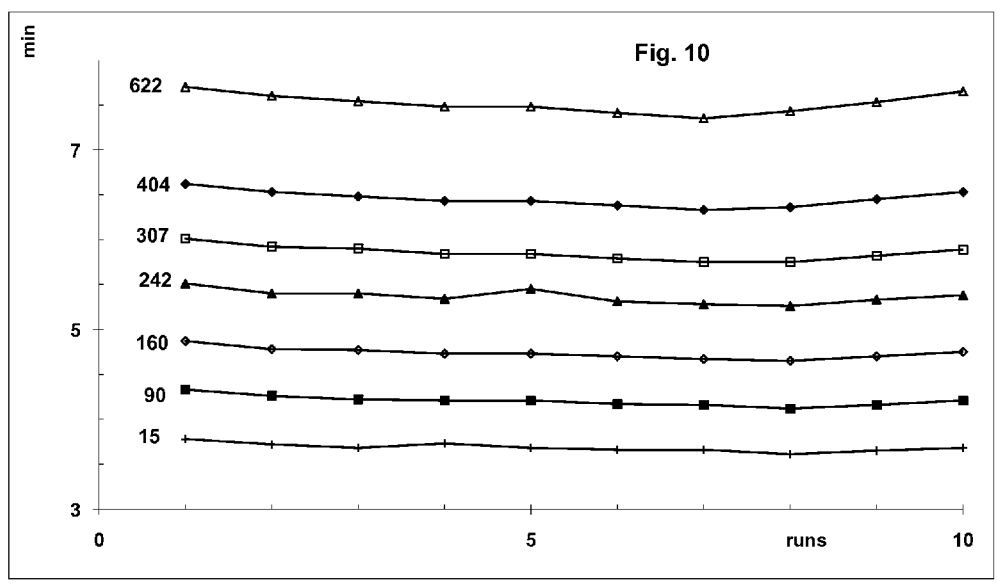
FIG. 10 shows reproducibility of migration times of selected pBR322 MspI restriction fragments on glass microchip without any matrix refill. For experimental conditions see FIG. 9.

Reproducibility of the migration times ranged from 1.29% to 1.54%. When the separation medium was kept in the channels of the chip and only the content of the electrode vials was replaced with fresh solution (Table 1.). Migration times of selected fragments are shown in FIG. 10.

TABLE 1

Reproducibility of migration times of pBR322 MspI restriction fragments (n = 10)

| bp | Average [min] | SD | RSD [%] |
|---|---|---|---|
| 15 | 3.69 | 0.05 | 1.29 |
| 26 | 3.79 | 0.06 | 1.51 |
| 34 | 3.85 | 0.05 | 1.36 |
| 67 | 4.04 | 0.05 | 1.33 |
| 76 | 4.11 | 0.06 | 1.41 |
| 90 | 4.21 | 0.06 | 1.41 |
| 110 | 4.36 | 0.06 | 1.37 |
| 123 | 4.46 | 0.06 | 1.34 |
| 147 | 4.64 | 0.07 | 1.42 |
| 160 | 4.74 | 0.06 | 1.33 |
| 180 | 4.89 | 0.07 | 1.42 |
| 196 | 4.96 | 0.07 | 1.40 |
| 201 | 5.05 | 0.07 | 1.37 |
| 217 | 5.18 | 0.07 | 1.35 |
| 238 | 5.32 | 0.07 | 1.29 |
| 242 | 5.37 | 0.08 | 1.44 |
| 307 | 5.85 | 0.08 | 1.39 |
| 404 | 6.45 | 0.09 | 1.45 |
| 527 | 7.10 | 0.11 | 1.48 |
| 622 | 7.51 | 0.12 | 1.54 |

Example 5

Figure 11:
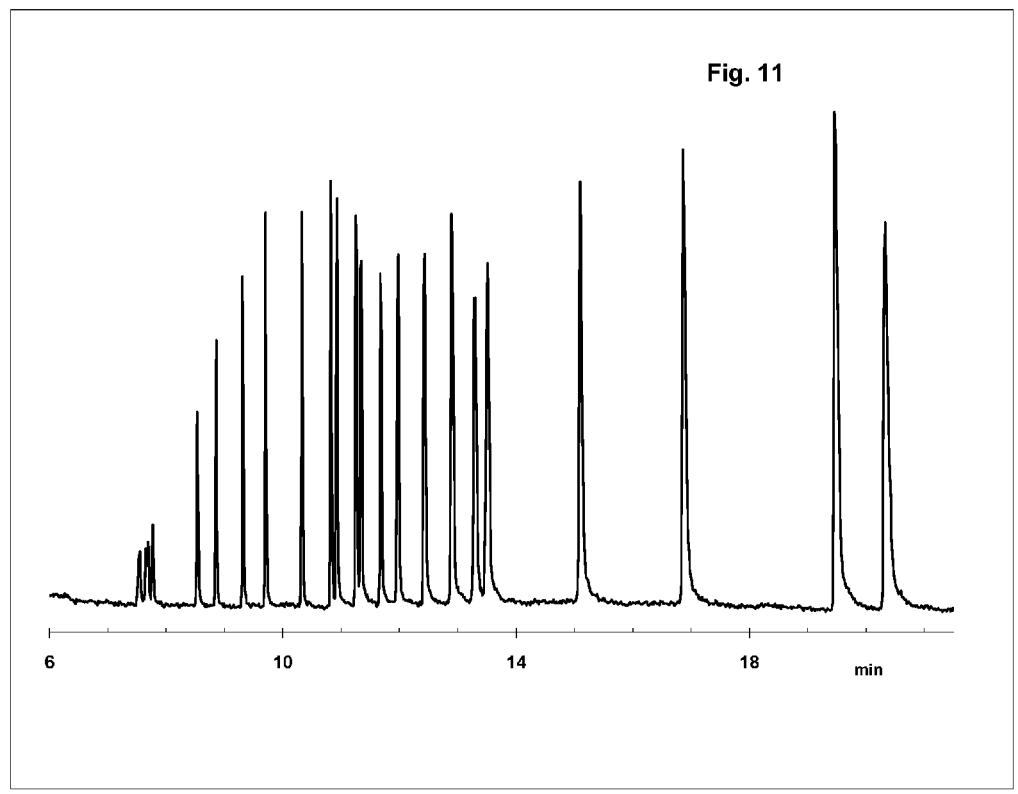
FIG. 11 shows a separation of pBR322 MspI restriction fragments in imidazole borate buffer. Separation medium: 12 g/L HEC, 0.8 M DMSO, 0.8 M imidazole borate, 1×SYBR Green II. Bare capillary, total length=40 mm, effective length=20 mm, ID=75 μm, OD=360 μm. Voltage: −8 kV. LIF detection: 488 nm excitation, 530 nm emission. Electrokinetic injection: 2 s at −8 kV. Sample: pBR322 MspI restriction fragments in 10 mM Tris-HCl, pH 8.0 (New England BioLabs, Inc.) diluted 5× with 0.1 M Tris HEPES. For peak identification, see FIG. 5.

Electrophoretic Separation of DNA Fragments in HEC with Imidazole Borate Buffer Imidazole borate as BGE suppressed electroosmotic flow and improved resolution of DNA separation by capillary sieving electrophoresis (FIG. 11. The pBR322 MspI restriction fragments were fully separated in a bare capillary filled with 12 g/L hydroxyethyl cellulose (HEC), 0.8 M DMSO, 800 mM imidazole borate buffer, and 1×SYBR Green II. All fragments were resolved, fragment pairs having 147 bp and 160 bp were separated with almost baseline resolution. (For the peak identifications, see FIG. 5) This example indicates a concentrated borate buffer can effectively suppress electroosmotic flow in the absence of polyol counter ion, particularly when the sieving polymers contribute to electroosmotic flow suppression.

Example 6

Electrophoretic Separation of DNA Fragments in HEC with Tris Borate Buffer

Figure 12:
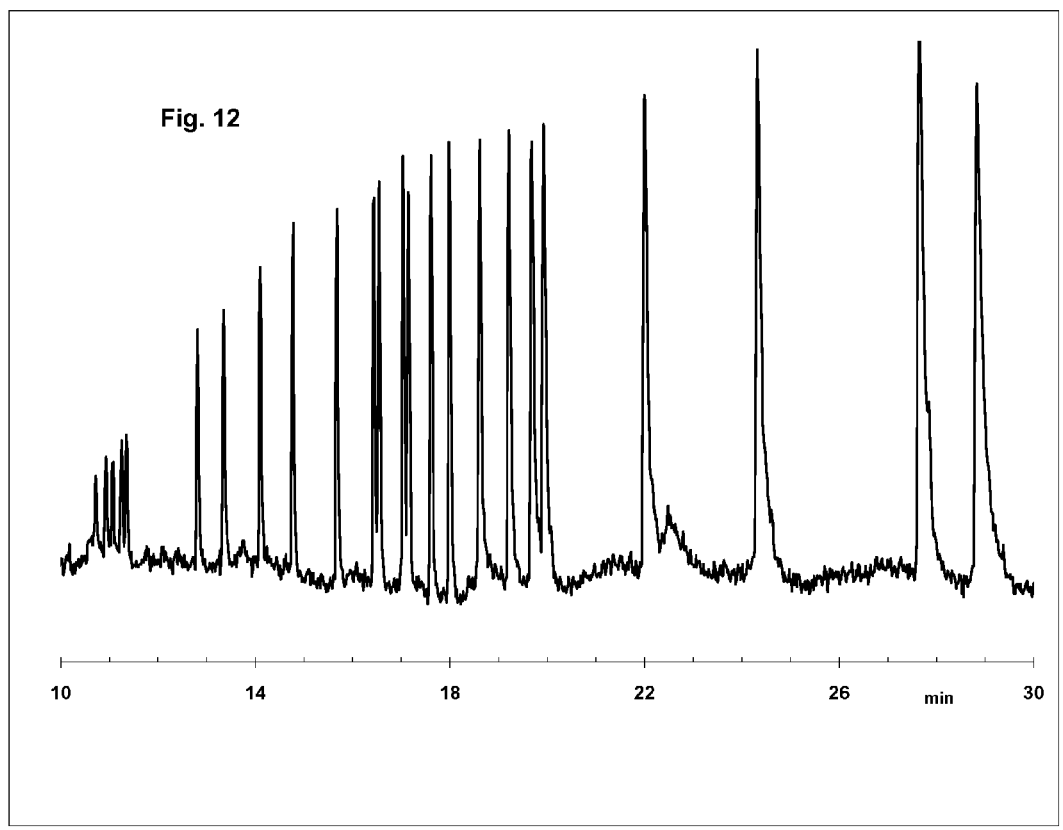
FIG. 12 shows a separation of pBR322 MspI restriction fragments in Tris borate buffer. Separation medium: 12 g/L HEC, 0.8 M DMSO, 0.1 M Tris, 1.0 M boric acid, 1×SYBR Green II. Bare capillary, total length=40 mm, effective length=20 mm, ID=75 μm, OD=360 μm. Voltage: −8 kV. LIF detection: 488 nm excitation, 530 nm emission. Electrokinetic injection: 2 s at −8 kV. Sample: pBR322 MspI restriction fragments in 10 mM Tris-HCl, pH 8.0 (New England BioLabs, Inc.) diluted 5× with 0.1 M Tris HEPES. For peak identification, see FIG. 5.

The separation of pBR322 MspI restriction fragments in a bare capillary filled with 12 g/L hydroxyethyl cellulose (HEC), 0.8 M DMSO, 100 mM Tris, 1.0 M borate buffer, and 1×SYBR Green II is shown in FIG. 12. All fragments were resolved, fragment pairs having 147 bp and 160 bp were separated with almost baseline resolution. (For the peak identifications, see FIG. 5).

Example 7

Electrophoretic Separation of DNA Fragments in HEC with Lithium Borate Buffer

Figure 13:
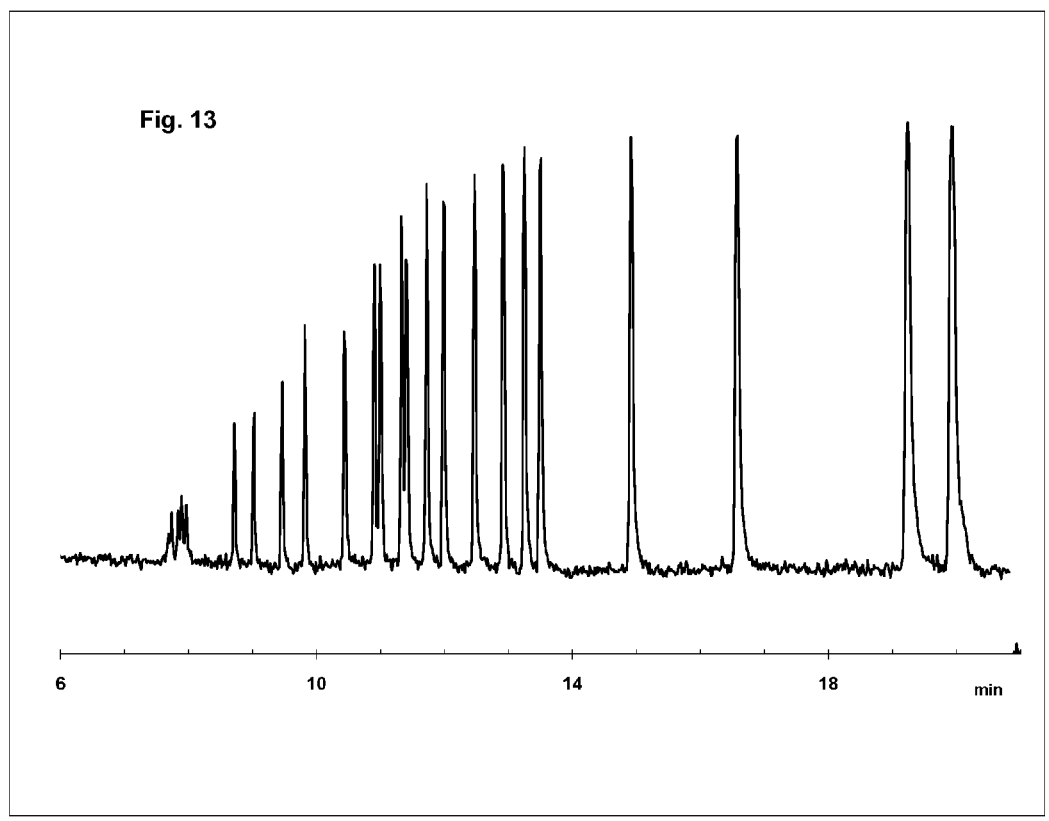
FIG. 13 shows a separation of pBR322 MspI restriction fragments in Li borate buffer. Separation medium: 12 g/L HEC, 0.8 M DMSO, 0.05 M LiOH, 1 M boric acid, 1×SYBR Green II. Bare capillary, total length=40 cm, effective length=20 cm, ID=75 μm, OD=360 μm. Voltage: −8 kV. LIF detection: 488 nm excitation, 530 nm emission. Electrokinetic injection: 1 s at −8 kV. Sample: pBR322 MspI restriction fragments in 10 mM Tris-HCl, pH 8.0 (New England BioLabs, Inc.) diluted 10× with 0.1 M Tris HEPES. For peak identification, see FIG. 5.

The separation of pBR322 MspI restriction fragments in a bare capillary filled with 12 g/L hydroxyethyl cellulose (HEC), 0.8 M DMSO, 50 mM LiOH, 1 M boric acid, and 1×SYBR Green II is shown in FIG. 13. All fragments were resolved, fragment pairs having 147 bp and 160 bp were separated with almost baseline resolution. (For the peak identifications, see FIG. 5). This example indicates a concentrated borate buffer can effectively suppress electroosmotic flow even if a strong base such as lithium is the only counter ion. Its concentration is to be rather low to keep the BGE conductivity at a level allowing high separation voltage.

Example 8

Figure 14:
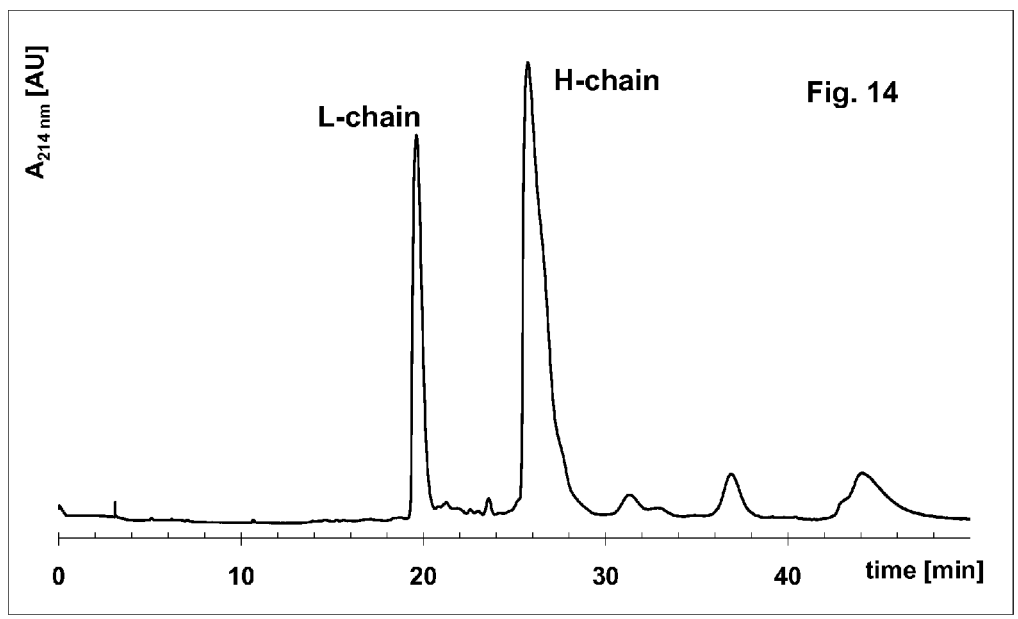
FIG. 14 shows a separation of L & H chains by SDS electrophoresis in 0.3 M Tris, 1.2 M boric acid. Separation medium: 100 g/L dextran ($M_w$ 2×10$^6$), 0.3 M Tris, 1.2 M boric acid, 2 g/L SDS. Bare capillary, total length=335 mm, effective length=250 mm, ID=75 μm, OD=360 μm. Separation voltage: −12 kV. UV detection at 214 nm. Electrokinetic injection: 10 s at −10 kV. Sample: 15 g/L bovine IgG in 100 mM Tris HCl, 15 g/L DTT, 10 min incubation at 70° C.

SDS Capillary Sieving Electrophoresis of Bovine γ-Globulin in Dextran Matrix with Tris Borate Buffer L-chain and H-chain were separated in a bare capillary filled with a sieving matrix containing 100 g/L dextran ($M_w$ 2×10$^6$), 0.3 M Tris, 1.2 M boric acid, and 2 g/L SDS is shown in FIG. 14. It demonstrated the potential of Tris borate buffer above concentration previously used.

Example 9

Figure 15:
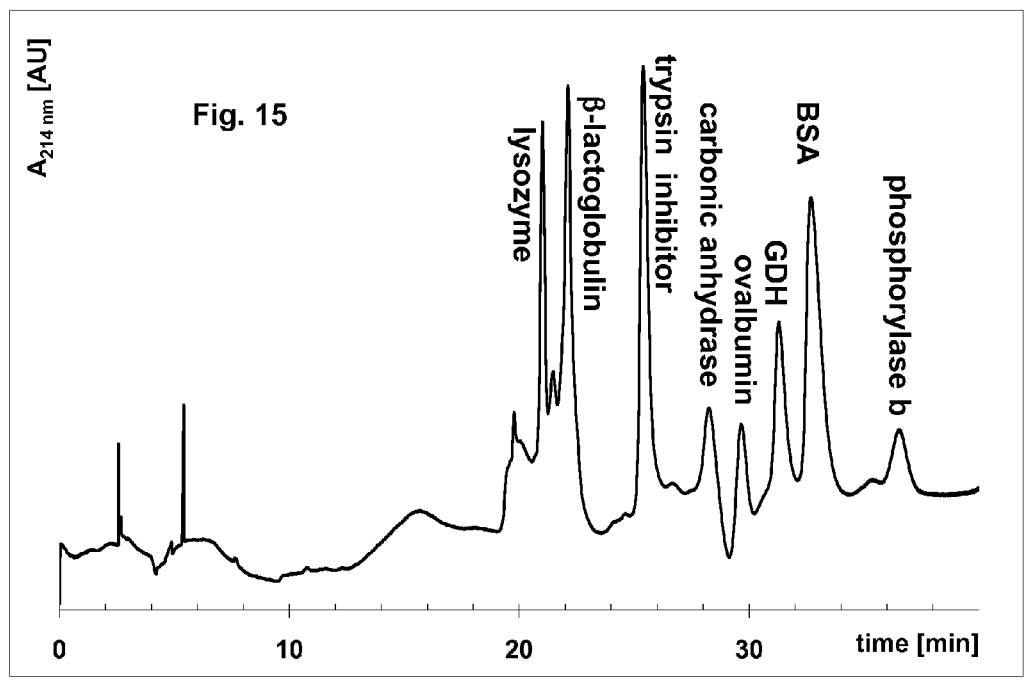
FIG. 15 shows separation of model proteins by SDS electrophoresis in 0.3 M Bis-Tris Propane borate. Separation medium: 100 g/L dextran ($M_w$ 2×10$^6$), 0.3 M Bis-Tris Propane borate, 2 g/L SDS, 100 g/L glycerol. Bare capillary, total length=335 mm, effective length=250 mm, ID=75 μm, OD=360 μm. Separation voltage: −20 kV, pre-run 10 min at −10 kV. UV detection at 214 nm. Electrokinetic injection: 10 s at −10 kV. Sample: 2 g/L proteins in 100 mM Tris-HCl, 15 g/L DTT, 10 min incubation at 70° C. (Abbreviations: CA—carbonic anhydrase, GDH— glutamate dehydrogenase, BSA—bovine serum albumin,)

SDS Capillary Sieving Electrophoresis of Model Proteins in Dextran Matrix with Bis-Tris Propane Borate Buffer Separation of molecular-weight standard proteins in a bare capillary filled with 100 g/L dextran ($M_w$ 2×10$^6$), 0.3 M Bis-Tris Propane, 0.3 M borate, 100 g/L glycerol, and 2 g/L SDS is shown in FIG. 15. The separation of the model proteins demonstrated the utility of other borate buffers to suppress electroosmotic flow and separate proteins by SDS capillary electrophoresis. It would be rather difficult to accurately describe all the equilibria where borate is involved. It interacts with 1) silica surface, 2) counter ion Bis-Tris Propane, 3) triol glycerol, 4) polysaccharide dextran, 5) glycoproteins such as ovalbumin. To optimize separation, the composition of the separation medium had to be fine-tuned.

Example 10

Figure 16:
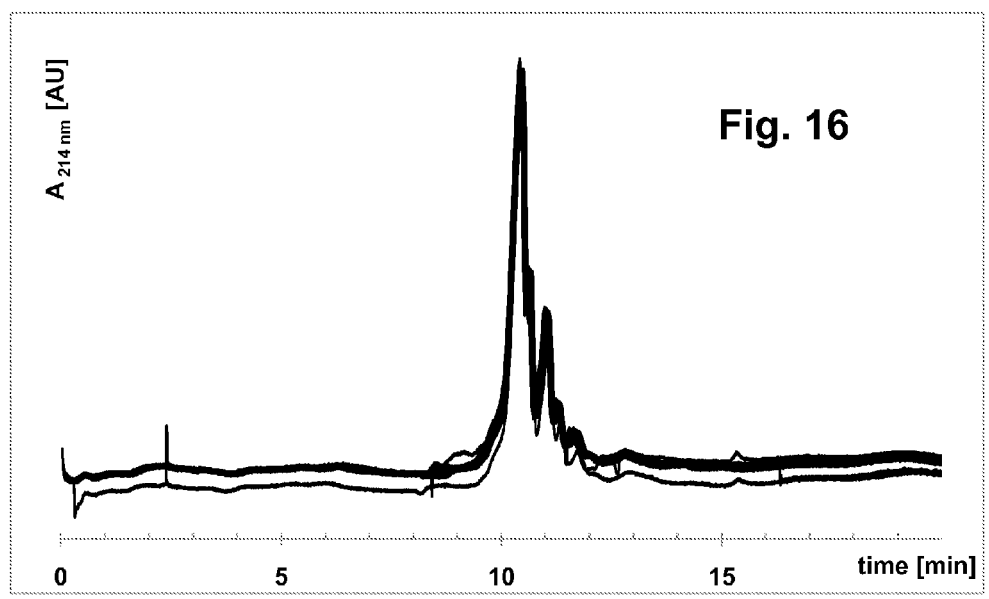
FIG. 16 shows 20 overlaid electropherograms showing CZE separation of ovalbumin isoforms. Separation medium: 0.2 M Bis-Tris Propane, 0.4M boric acid. Bare capillary, total length=335 mm, effective length=250 mm, ID=50 μm, OD=360 μM. Separation voltage: −15 kV. UV detection at 214 nm. Pressure injection: 5 s at 50 mbar. Sample: 10 g/L ovalbumin V in water.

Capillary Electrophoresis of Ovalbumin Isoforms in Bis-Tris Propane Borate Buffer Ovalbumin isoforms were separated into 5-7 major peaks by CZE in 200 mM Bis-Tris Propane, 400 mM borate (FIG. 16). The repeatability of migration times in 20 runs ranged from 0.3% to 0.43% (Table 2).

TABLE 2

Reproducibility of migration times of ovalbumin isoforms (n = 20)

| Peak | Average [min] | SD | RSD [%] |
|---|---|---|---|
| 1 | 10.433 | 0.031 | 0.29 |
| 2 | 10.631 | 0.032 | 0.30 |
| 3 | 11.017 | 0.034 | 0.31 |
| 4 | 11.273 | 0.038 | 0.33 |
| 5 | 11.665 | 0.050 | 0.43 |

The invention claimed is:

1. A separation medium for capillary sieving electrophoresis comprising:
    a) a neutral hydrophilic polymer at the concentration from about 0 g/L to about 200 g/L;
    b) a neutral polyol at the concentration from about 20 g/L to about 200 g/L;
    c) a biopolymer denaturant at the concentration from about 0 g/L to about 420 g/L;
    d) a cationic counter ion at the concentration between about 0.02 M and about 3 M;
    e) boric acid at the concentration from about 0.1 M and about 3 M, with the proviso that
        1) if said biopolymer denaturant is SDS and said counter ion is Tris the concentration of boric acid is in the range from about 1.1 M to about 3 M;
        2) if said counter ion is sodium the concentration of boric acid is in the range from about 0.8 M to about 3 M.

2. A separation medium for capillary sieving electrophoresis of claim 1, wherein said neutral hydrophilic polymer is selected from the group of polymers consisting of hydroxyethyl cellulose, hydroxypropyl cellulose, hydroxyisopropyl cellulose, locust bean gum, tara gum, guar gum, hydroxyisopropyl guaran, fenugreek gum, konjac, pullulan, pustulan, agarose, laminaran, dextran, amylose, schyzophyllan, nigeran, poly(vinyl alcohol), poly(vinyl pyrrolidone), poly(ethylene oxide), poly(dimethyl acrylamide), and polyacrylamide.

3. A separation medium for capillary electrophoresis of claim 1, wherein said biopolymer denaturants are selected from the group of denaturants consisting of urea, thiourea, formamide, methyl formamide, dimethyl formamide, ethyl formamide, dimethyl sulfoxide, sodium dodecyl sulfate, lithium dodecyl sulfate, sodium lauroyl sarcosinate, sodium decyl sulfate, and lauric acid.

4. A separation medium for capillary electrophoresis of claim 1, wherein said neutral polyol is selected from the group of polyols consisting of glycerol, ethylene glycol, mannitol, sorbitol, dulcitol, ribitol, maltitol, fucitol, erythritol, xylitol, arabitol, erythrose, threose, erythrulose, ribose, arabinose, xylose, lyxose, ribulose, xylulose, glucose, fructose, galactose, mannose, saccharose, lactose, maltose, maltotriose, and dextrin.

5. A separation medium for capillary electrophoresis of claim 1, wherein said cationic counter ion is selected from the group of bases consisting of lithium, sodium, arginine, lysine, histidine, imidazole, methylimidazole, morpholine, ethylmorpholine, tris(hydroxymethyl)aminomethane, tris(hydroxymethyl)ethane, tris(hydroxymethyl)propane, bis-(2-hydroxyethyl)-amino-tris(hydroxymethyl)-methane (Bis-Tris), 1,3-bis[tris(hydroxymethyl)methylamino]propane (Bis-Tris Propane), 2-amino-2-methylpropane-1,3-diol (Ammediol), ethanolamine, diethanolamine, triethanolamine, triisopropanolamine, N-methylglucamine, glucosamine, galactosamine, and fructosamine.

6. A separation medium for capillary electrophoresis of claim 1, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is from about 0.1 M to about 0.5 M triethanolamine and boric acid is present at the concentration from about 0.4 M to about 1 M.

7. A separation medium for capillary electrophoresis of claim 1, wherein said neutral hydrophilic polymer is from about 5 g/L to about 60 g/L polyacrylamide, said biopolymer denaturant is from about 0.1 M to about 2 M dimethyl sulfoxide, said counter ion is from about 0.1 M to about 0.5 M triethanolamine and boric acid is present at the concentration of from about 0.4 M to about 1 M.

8. A separation medium for capillary electrophoresis of claim 1, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is Tris and boric acid is present at the concentration of from about 0.4 M to about 1 M.

9. A separation medium for capillary electrophoresis of claim 1, wherein said neutral hydrophilic polymer is from about 5 g/L to about 60 g/L polyacrylamide, said biopolymer denaturant is from about 0.1 M to about 2 M dimethyl sulfoxide, said counter ion is about 0.1 M Tris and boric acid is present at the concentration of about 1 M.

10. A separation medium for capillary electrophoresis of claim 1, wherein said neutral hydrophilic polymer is from about 5 g/L to about 60 g/L hydroxyethyl cellulose, said biopolymer denaturant is from about 0.1 M to about 2 M dimethyl sulfoxide, said counter ion is about 0.1 M Bis-Tris Propane, and boric acid is present at the concentration of about 1 M.

11. A separation medium for capillary electrophoresis of claim 1, wherein said neutral hydrophilic polymer is from about 5 g/L to about 60 g/L hydroxyethyl cellulose, said biopolymer denaturant is from about 0.1 M to about 2 M dimethyl sulfoxide, said neutral polyol is from about 20 g/L to 200 g/L mannitol, said counter ion is about 0.1 M Bis-Tris Propane, and boric acid is present at the concentration of about 1 M.

12. A separation medium for capillary electrophoresis of claim 1, wherein said neutral hydrophilic polymer is from about 5 g/L to about 60 g/L hydroxyethyl cellulose, said biopolymer denaturant is from about 0.1 M to about 2 M dimethyl sulfoxide, said neutral polyol is from about 20 g/L to 200 g/L glycerol, said counter ion is about 0.1 M Bis-Tris Propane, and boric acid is present at the concentration of about 1 M.

13. A separation medium for capillary electrophoresis of claim 1, wherein said neutral hydrophilic polymer is about 16 g/L hydroxyethyl cellulose, said biopolymer denaturant is about 0.8 M dimethyl sulfoxide, said neutral polyol is about 0.5 M sorbitol, said counter ion is about 0.4 M Bis-Tris Propane, and boric acid is present at the concentration of about 0.2 M.

14. A separation medium for capillary electrophoresis of claim 1, wherein said neutral hydrophilic polymer is about 16 g/L hydroxyethyl cellulose, said biopolymer denaturant is about 0.8 M dimethyl sulfoxide, said neutral polyol is about 0.5 M sorbitol, said counter ion is about 0.4 M Tris, and boric acid is present at the concentration of about 0.4 M.

15. A separation medium for capillary electrophoresis of claim 1, wherein said counter ion is about 0.2 M Bis-Tris Propane, and boric acid is present at the concentration of about 0.4 M.

16. A separation medium for capillary electrophoresis of claim 1, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is from about 0.1 M to about 0.6 M Bis-Tris Propane, and boric acid is present at the concentration from about 0.2 M to about 1 M.

17. A separation medium for capillary electrophoresis of claim 1, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L mannitol, said counter ion is from about 0.1 M to about 0.6 M Bis-Tris Propane, and boric acid is present at the concentration from about 0.2 M to about 1 M.

18. A separation medium for capillary electrophoresis of claim 1, wherein said neutral hydrophilic polymer is about 100 g/L dextran ($M_w$ $2\times10^6$), said biopolymer denaturant is about 2 g/L sodium dodecyl sulfate, said neutral polyol is about 100 g/L mannitol, said counter ion is about 0.3 M Bis-Tris Propane, and boric acid is present at the concentration of about 0.3 M.

19. A separation medium for capillary electrophoresis of claim 1, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is about 0.3 M Tris, and boric acid is present at the concentration of about 1.2 M.

20. A separation medium for capillary electrophoresis of claim 1, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L glycerol, said counter ion is from about 0.2 M to about 0.6 M triethanolamine, and boric acid is present at the concentration from about 0.2 M to about 0.6 M.

21. A separation medium for capillary electrophoresis of claim 1, wherein said neutral hydrophilic polymer is from about 40 g/L to about 120 g/L dextran, said biopolymer denaturant is from about 0.1 g/L to about 5 g/L sodium dodecyl sulfate, said neutral polyol is from about 20 g/L to about 200 g/L mannitol, said counter ion is from about 0.2 M to about 0.6 M triethanolamine, and boric acid is present at the concentration from about 0.2 M to about 0.6 M.

22. A procedure for capillary electrophoresis performed in a separation channel, said separation channel made in an insulating body, said insulating body selected from the group consisting of fused silica capillary, fused silica chip, silicon chip, glass chip, poly(methyl methacrylate) chip, polycarbonate chip, and cyclic polyolefin chip, wherein said procedure comprises following steps:
  a) flushing said separation channel with about 0.1 M HCl;
  b) filling said separation channel with said separation medium for capillary electrophoresis of claim 1;
  c) injecting a sample into said separation channel;
  d) separating components of said sample by applying electric voltage; and
  e) detecting said separated components of said sample online.

* * * * *